United States Patent [19]

Lee

[11] 4,126,938
[45] Nov. 28, 1978

[54] JAW MOVEMENT SIMULATION

[76] Inventor: Robert L. Lee, 22937 Grand Terrace Rd., Colton, Calif. 92324

[21] Appl. No.: 742,977

[22] Filed: Nov. 18, 1976

Related U.S. Application Data

[62] Division of Ser. No. 485,158, Jul. 1, 1974, Pat. No. 4,034,474.

[51] Int. Cl.² .............................................. A61C 9/00
[52] U.S. Cl. ......................................................... 32/20
[58] Field of Search ................................ 32/19, 20, 21

[56] References Cited

U.S. PATENT DOCUMENTS 2,814,876  12/1957  Stuart ..................................... 32/19

Primary Examiner—Robert Peshock
Attorney, Agent, or Firm—Knobbe, Martens, Olson, Hubbard & Bear

[57] ABSTRACT

An upper frame including parallel side arms is supported on the patient's ears and attached to a transverse rod supported on the bridge of the patient's nose. A record plate depends from each side arm overlying each of the patient's temporomandibular joints. A lower frame is attached to the lower jaw by means of an adjustable clutch. Adjustable side arms carrying movable styluses engage the record plates on the upper frame. Movement of the styluses over the record plates is monitored to obtain measurements of the joint movements. A tooth separator swingably mounted on the transverse rod of the lower frame separates the rear teeth slightly when the jaw movements are being measured. After the hinge axis position has been located on the record plates, an adjustable straight edge is utilized to indicate the true horizontal plane of reference formed by the two hinge axis points and the point on the patient's nose. The stylus movements can be monitored mechanically or electronically and the resulting measurements utilized to set an adjustable dental articulator or to select preformed motion analogue blocks having pathways for guiding the styluses of an articulator.

11 Claims, 23 Drawing Figures

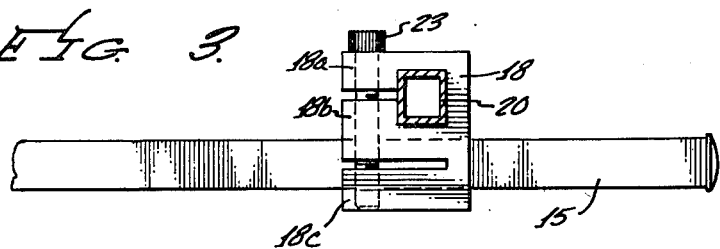
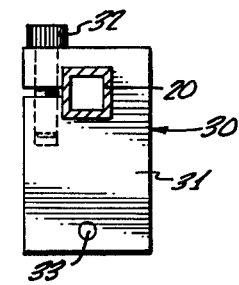
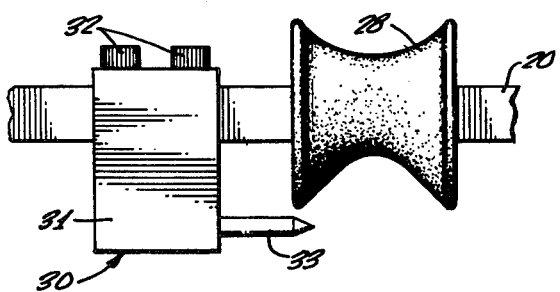
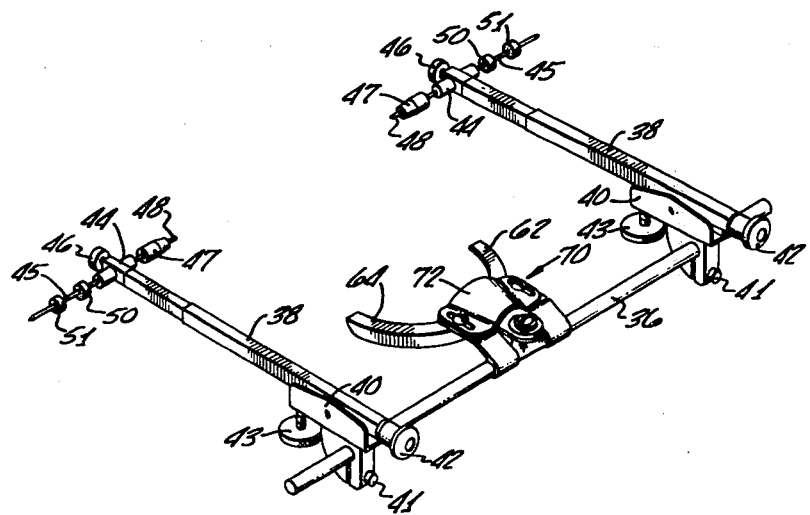

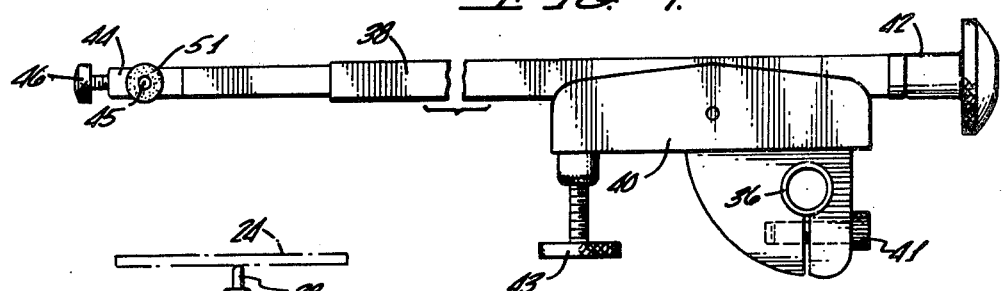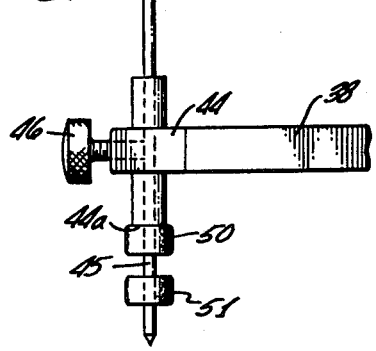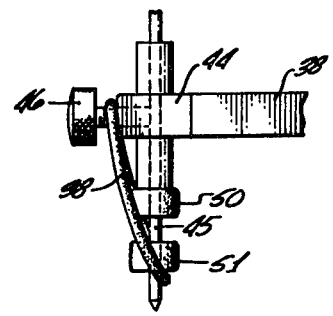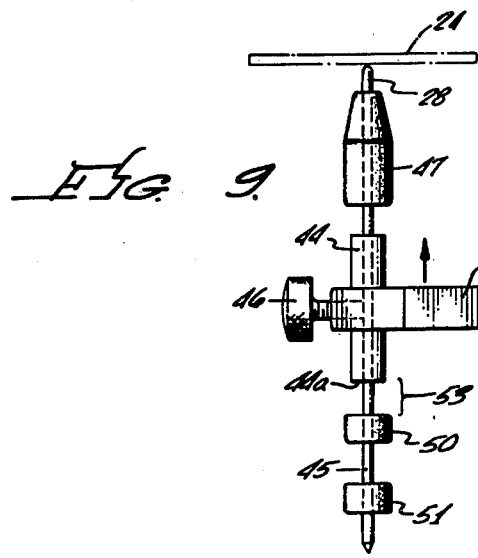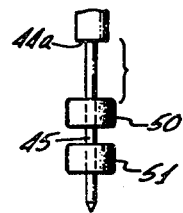

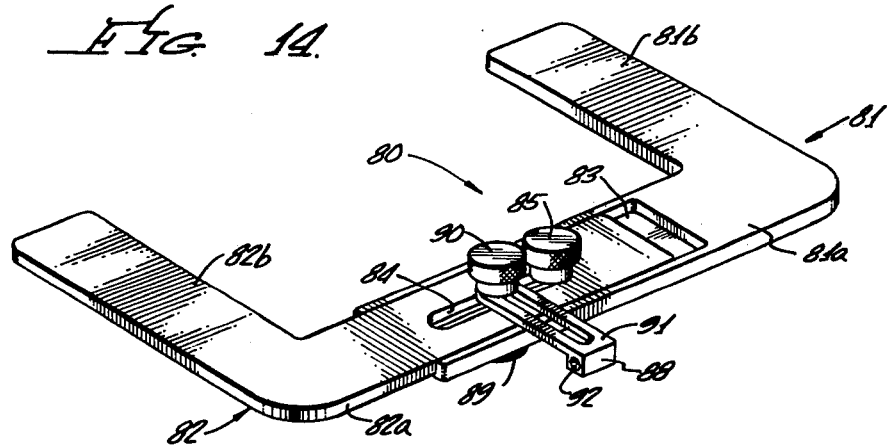
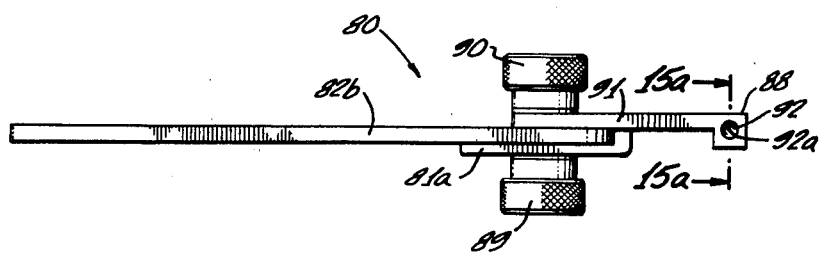
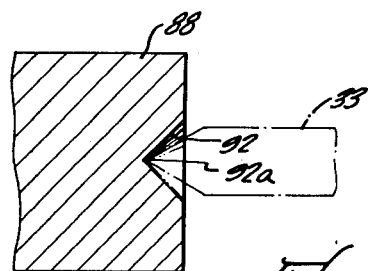

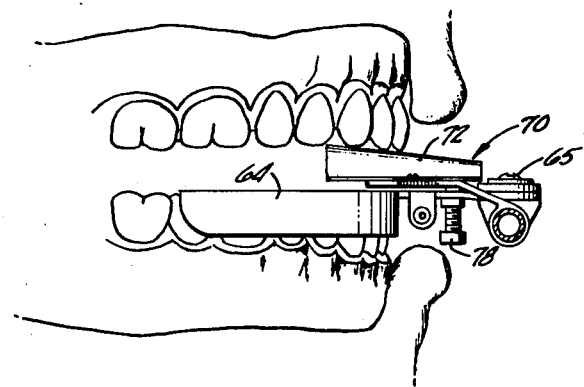
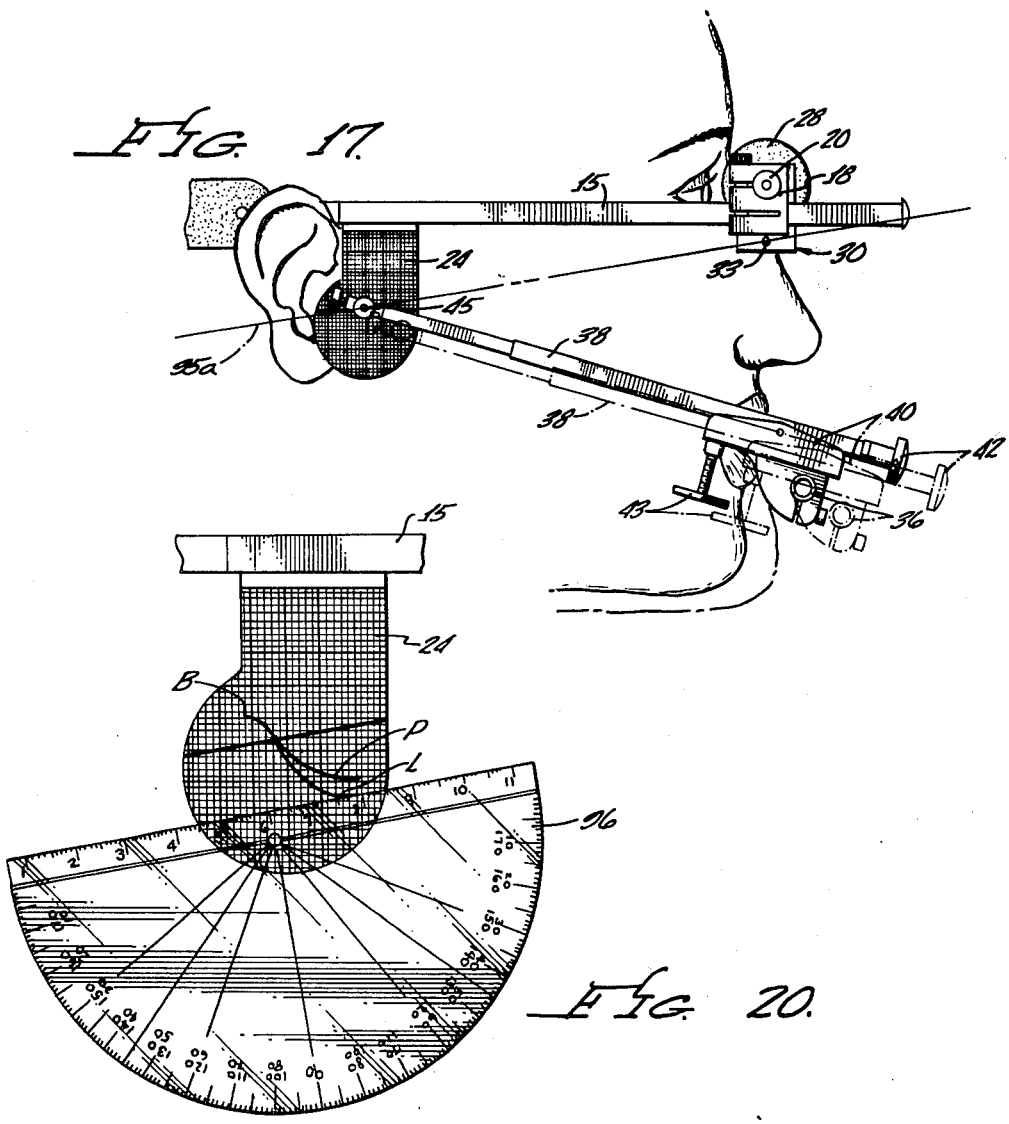

JAW MOVEMENT SIMULATION

This is a division of application Ser. No. 485,158, filed July 1, 1974 and now U.S. Pat. No. 4,034,474 issued July 12, 1977.

This invention relates to jaw movement simulation and more particularly to improvements in apparatus for recording or analyzing jaw movements and the methods of utilizing such apparatus to measure jaw movements. The invention further relates to a system for obtaining simulated jaw joint action for use in a dental articulator by utilizing the jaw movement measurements obtained through the use of the apparatus.

In the making of dental prostheses and in the analyzing and treatment of other jaw disorders, it is desirable to have means for simulating the individual patient's jaw movements. Consequently, a variety of dental articulators have been developed for such purposes. While these are useful instruments with varying degrees of accuracy of simulation, they all only provide fairly rough approximations of the patient's actual temporomandibular joints. The shortcomings of these devices in this regard are discussed extensively in U.S. Pat. No. 3,452,439, issued to Robert L. Lee, the same inventor as the present invention. In this patent there is disclosed a system for much more accurately simulating if not actually duplicating a patient's jaw movements. Briefly, the system disclosed therein records jaw movements in solid plastic record blocks. The information stored in these blocks is then transferred by transfer apparatus to prepare a second set of plastic blocks in which are formed guide pathway openings which closely simulate or duplicate the patient's jaw joint movements. These "analogue" blocks are then mounted in a dental articulator to simulate the patient's jaw movements. The walls of the openings in these analogue blocks are three-dimensional and control movement in the six degrees of freedom.

While the system disclosed in the aforementioned Lee patent is highly accurate and therefore a very significant contribution to this field, it is relatively costly to obtain a set of analogue blocks through this system. There are many steps to follow in the procedure which take considerable time and skill such that normally the work must be done by a dentist, who requires considerable training to become adept at the procedure. In effect, it is a very precise and personalized procedure to obtain a set of custom-made guide blocks for reproducing jaw movements. Consequently, the system has not been widely used being largely limited to research and larger dental schools in that the cost and complexity is more than the usual dentist can justify, and more costly than the patient is willing or capable of paying. Therefore, a need exists for simplifying and reducing the cost of obtaining jaw movements while still maintaining acceptable accuracy.

The present invention accomplishes this by introducing several improvements in apparatus and the method of utilizing this apparatus and other available equipment. As one step in the procedure, it is necessary that certain information regarding the patient's jaw movement be obtained and such information should be obtained relatively quickly and easily and yet accurately. Thus there is provided improved apparatus including a maxillary frame having a pair of side arms with a rigid recording plate perpendicularly mounted on each of the arms to be positioned over the hinge axis of the patient's temporomandibular joints. Also provided is a lower frame which is fixed to the patient's mandible and which has a stylus or transducer probe mounted to engage each of the two recording plates on the maxillary frame to monitor or record mandibular movements.

By utilizing a pair of writing elements as styluses for engaging a paper grid on the recording plates, a curve or line may be traced directly on the grids when the patient's mandible moves from centric relation position to a protrusive position. From this recorded curve various information may be obtained relating to the configuration of the movement of the jaw joints. For example, one important parameter which can be measured is the slope of descent with respect to a horizontal plane of reference. This horizontal reference plane is formed from a point on the nose and the hinge axis line in centric relation position. By means of a special adjustable straight edge tool mounted on the upper frame, the horizontal reference plane may be scribed on the two vertical record plates. The angles can be measured with a suitable tool such as a protractor.

Another parameter of condyle movements relative to the upper jaw is the side shift. This includes both the so-called immediate side shift, progressive side shift and total side shift. Such information is obtained by a displacement technique involving the lower frame apparatus. The styluses on the lower frame which engage the grids on the upper frame are movably mounted on the side arms of the lower frame. Thus these styluses may be slid into engagement with the grids when the patient's mandible is in centric position and the styluses locked in such position. A suitable marker is mounted on the outer end of the stylus with its inner or medial side in engagement with the structure supporting the stylus, or other suitable reference surface. The styluses are then unlocked and the patient's mandible is moved to one side (as in chewing) to the extent possible to demonstrate any immediate side shift of the condyles. This motion will cause the stylus mountings on the side opposite to the direction the jaw moves to slide inwardly on its stylus because the stylus inner end is in engagement with the stationary grid on the upper frame apparatus. The marker on the stylus becomes correspondingly spaced from the reference surface. Thus it is a simple matter to measure the distance between the reference surface and the marker, which represents the displacement of the stylus and the condylar side shift. The characteristics of the side shift timing can also be observed as to whether the side shift is immediate, progressive, nonprogressive, or both immediate and progressive, or does not exist at all.

Again, these measurements may be performed entirely mechanically and manually or they may be monitored and measured electronically.

While measuring these jaw movements, it is important that the patient's teeth not restrict the full range of movement so that the characteristics of the joints may be determined as accurately as possible. Further it is particularly important that the patient's mandible be easily and repeatedly movable into centric relation position. Hence the patient's rear teeth should be slightly separated during such movement. The prior art discloses a rather cumbersome procedure for obtaining such separation which involves fabricating clutches for both the mandible and maxilla. The present invention employs a simplified tooth separator which is mounted on the lower frame in a manner such that the patient's upper front teeth or ridges can simply rest on the separator. Also the separator is conveniently mounted to be quickly moved out of the patient's mouth so that the operator can easily place or remove the clutch from the teeth. The separator is adjustable in several respects to accommodate various jaw sizes and relationships.

More specifically, the tooth separator is pivotally mounted on a transverse rod on the lower frame which is the same rod supporting the side arms of the frame. The frame is attached to the patient's lower jaw by means of an adjustable clutch mounted on a strut which in turn is connected to the transverse rod. An adjustable screw extends through the strut and engages a lower surface on the tooth separator to provide vertical adjustment for the separator.

The information obtained by utilizing the above described apparatus and methods can be employed for adjusting various dental articulators and thus the apparatus and methods are useful just for that reason alone. The information may also be used with the more accurate preformed analogue guide blocks described above in connection with the aforementioned Lee patent, and as described in the above-identified parent application.

Further features and advantages of the invention will be apparent by reference to the following detailed description and drawings in which:

FIG. 3 is a cross-sectional view taken along the lines 3—3 of FIG. 2 to illustrate the mounting of the transverse rod of the upper frame with respect to the side arms;

FIG. 4 is a cross-sectional view on lines 4—4 of FIG. 2 illustrating the mounting of the nose pointer;

FIG. 5 is a front elevational view of the nose pointer;

FIG. 6 is a perspective view of the lower frame apparatus;

FIG. 7 is a side elevational view of the lower frame apparatus;

FIG. 8 is a plan view of one of the styluses of the lower frame in engagement with the record plate of the upper frame with the side movement marker in its initial position;

FIG. 8a is a view like FIG. 8 with the stylus being urged against the record plate by an elastic band;

FIG. 9 is a view like FIG. 8 after the lower frame except the stylus holder has been shifted sideways on the stylus away from its marker in response to immediate side movement of the patient's mandible;

FIG. 9a is a fragmentary view of FIG. 9 showing the displacement for full side shift;

FIG. 14 is a top perspective view of a tool for locating the exact horizontal plane of reference formed by the jaw hinge axis and a point on the patient's nose;

FIG. 15 is a side elevational view of the tool of FIG. 14;

FIG. 15a is a cross-sectional view of the dimple of FIG. 15;

FIG. 16 is a side elevational view of a patient with the tooth separator in use;

FIG. 17 is a side elevational view of the recording frames in use on the patient's head and with the protrusive movement of the mandible shown in phantom lines;

FIG. 20 is an enlarged view of a record plate with the plane of reference and the movement curves marked thereon, and a protractor for measuring the curve angle from this plane.

Upper Head Frame

Figure 1:
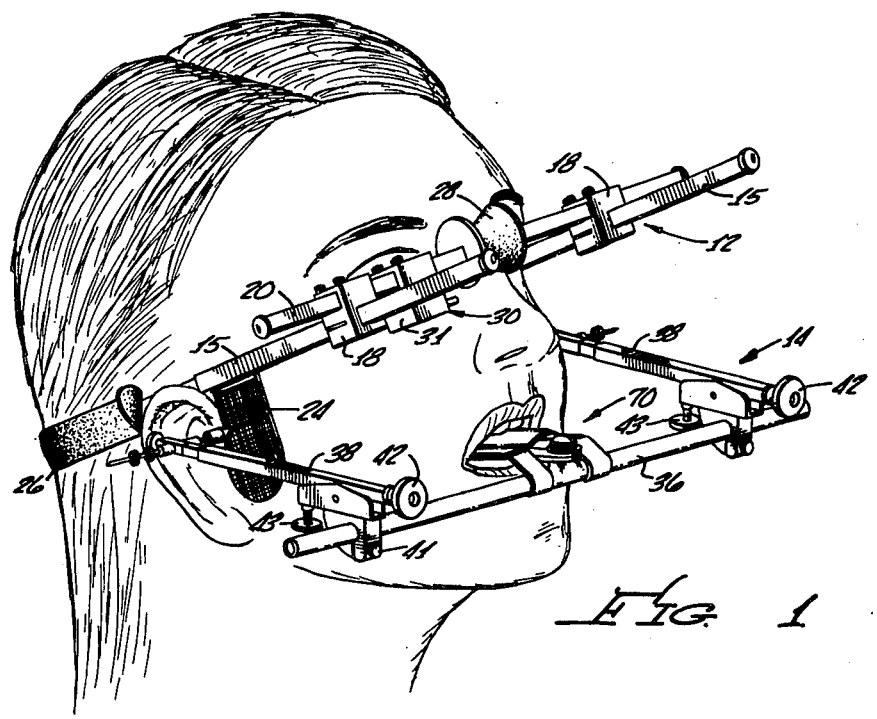
FIG. 1 is a perspective view illustrating the apparatus of the invention mounted on a patient.
Figure 2:
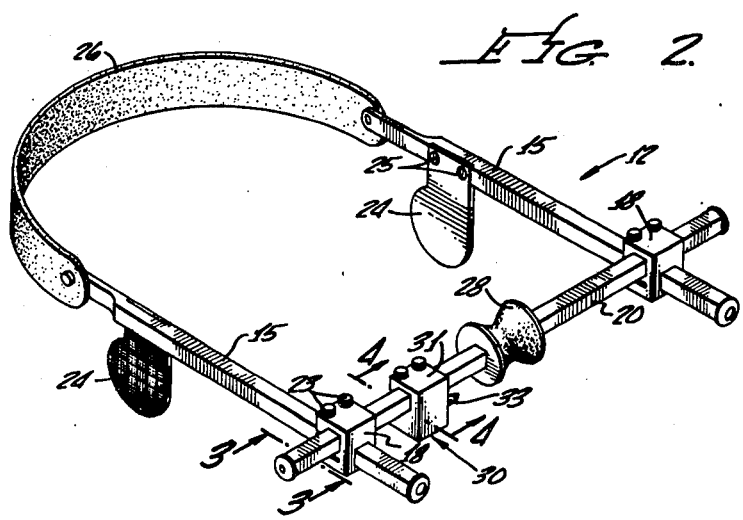
FIG. 2 is a perspective view of the upper frame apparatus.

Referring first to FIG. 1 there is shown an upper frame 12 and a lower frame 14 mounted on a patient's head 10. As can be seen the upper frame is mounted on the patient's nose and ears, while the lower frame is attached to the patient's lower jaw. Referring to FIG. 2, it may be seen that the upper frame apparatus includes a pair of side arms 15 formed of rigid materials such as metal or plastic and having a square cross-section. The side arms 15 are slidably mounted in support blocks 18. A transverse rod 20 is also slidably mounted in the support block 18 in perpendicular relation to the side arms 15. As can be seen from FIG. 3, the transverse rod 20 also has a square cross-section so that it is permanently held in perpendicular relation to the side arms even though the side arms may be moved forwardly and rearwardly to be suitably adjusted on the patient's ears and may be moved sideways to fit the width of the patient's head. Suitable clamping screws 22 and 23 extend through the block 18 to lock the side arms in a selected position. More specifically, the outer screw 22 clamps the upper and middle segment 18a and 18b (FIG. 3) of the clamp 18 to fix the side arms laterally with respect to the transverse rod 20 while the inner screw 23 clamps the upper and lower segments 18a and 18c to fix the rearward or forward movement of the side arms with respect to the transverse rod.

A stiff or rigid reference or recording plate 24 is attached to each of the side arms 15 adjacent the rear end of the arms by a pair of screws 25 or other suitable means. The plates are mounted in fixed perpendicular relation with respect to the arms 15 and 16 and extend downwardly to be positioned in front of the patient's ears as seen in FIG. 1. Each plate has a curved lower portion which extends rearwardly towards the ear so that the plate completely covers the area of the patient's temporomandibular joint when mounted on the patient's face as seen in FIG. 1. On the outer surface of each plate is a grid of intersecting lines which are perpendicular to each other, and therefore the vertical lines are perpendicular to the side arms 15 and 16 and the horizontal lines are parallel to the side arms. The grid may conveniently be formed on a separate sheet of paper held by adhesive to the plate in a manner such that the sheet is readily removable from the plate. A flexible strap 26 attached to the rear end of the side arms helps maintain the upper frame on the patient's head.

Mounted on the center of the transverse rod 20 is a nasion support 28 which rests on the bridge or nasion of the patient's nose. As can be seen from FIG. 5, the support 28 has a smoothly curved central section tapering to larger diameter flanges on the ends. The curvature of the support is not symmetrical and it may be rotated on the support 20 to best to conform to the patient's nasion.

Also mounted on the transverse rod 20 is a pointer assembly 30 comprising a mounting block 31 which is slidably mounted on the transverse rod 20. The mounting block 31 may be locked in a desired position by means of the screw 32 attached. A pointer 33 is mounted on the lower end of the block 31 extending generally parallel to the rod 20 towards the support 28. With this arrangement, it may be seen that the pointer is transversely adjustable on the rod 20 but remains fixed a preselected distance below the transverse rod 20 and parallel to the rod.

Lower Head Frame

Referring to FIG. 6, it may be seen that the lower head frame 14 includes a transverse rod 36 on which is mounted a pair of side arms 38. The side arms are each attached to the transverse rod 36 by a supporting unit 40 which keeps the side arms perpendicular to the transverse rod 36 while permitting them to be individually slid transversely on the rod and locked by means of a screw 41; individually moved rearwardly and forwardly by means of the adjusting screw 42; and moved angularly with respect to the transverse rod 36 by means of the adjusting screw 43 all as seen in FIGS. 6 and 7.

Positioned on the end of each of the side arms 38 is a tubular holder 44 which extends perpendicular to the side arm parallel to the transverse rod 20. A stylus, or axis pin, or other small diameter element 45 is slidably positioned in the tubular holder 44. A set screw 46 threads into the interior of the holder to lock the stylus in its desired position. On the inner end of the stylus 42 is mounted another tubular holder 46 in which is firmly positioned a scribe or writing element 48. The scribe 48 may be forcefully removed and replaced by another element or transducer. The entire stylus can be a writing element if desired.

On the outer end of the stylus 45 is slidably mounted a ring shaped marker 50 which is made of teflon, plastic or other suitable material which will grip the stylus 45 but yet may be manually slid on the stylus.

Clutch and Tooth Separator

Referring to FIGS. 10-13, a T-shaped support member 60 is mounted between two halves of the transverse rod 36. A pair of clutch pieces 62 and 64 are attached to the support 60 by means of a screw 65. As can be seen, each of the clutch pieces 62 and 64 includes strut portion whose forward end is attached to the support 60 and whose rearward end supports a curved portion adapted to fit over the lower teeth or gums of the patient. Each of the clutch strut portions includes a depending flange 62a and 64a. An adusting screw 66 is threadedly mounted in the flanges so that the spacing between the clutch pieces 62 and 64 is laterally adjustable by means of the screw 66.

Figure 11:
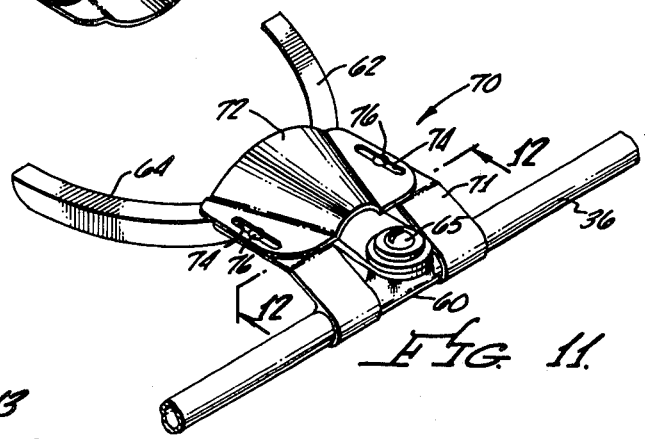
FIG. 11 illustrates the tooth separator in its operating position.
Figure 12:
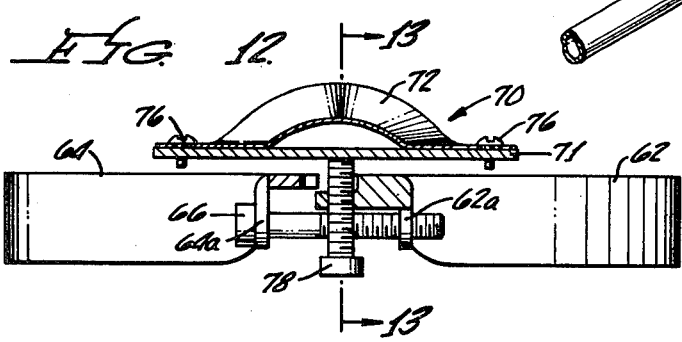
FIG. 12 is a cross-sectional view of the separator on lines 12—12 of FIG. 11 illustrating the vertical adjustment of the separator.
Figure 13:
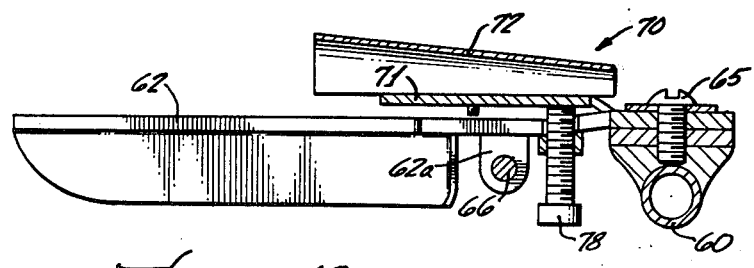
FIG. 13 is a side cross-sectional view on lines 13—13 of FIG. 12 further illustrating the configuration of the separator.

Pivotally mounted on the transverse rod 36 is a tooth separator base plate 70. More specifically, the base plate 70 includes a pair of arms straddling the clutch support member 60 and which fit over the transverse rod 36 so that the base plate is swingable about the rod. The base plate 70 further includes a flat portion on which is mounted a separator or contact element 72. The separator element has a pair of side flanges with elongated mounting slots 74 which receive screws 76 threaded into the separator base plate 70. This arrangement of course permits front to rear adjustment of the separator elements 72 with respect to the base plate 70. The upper surface of the separator element 72 is smoothly curved into an arch shape from side to side as seen in FIGS. 11 and 12. Also, as seen by FIG. 12, the element 72 slopes downwardly in the forward direction. The patient's upper teeth or gums engage the upper surface of the separator element 72. The height and shape of the arch may be selected to best fit the patient's mouth. Various separator elements may be employed since they are readily separable from the base plate 70.

Figure 10:
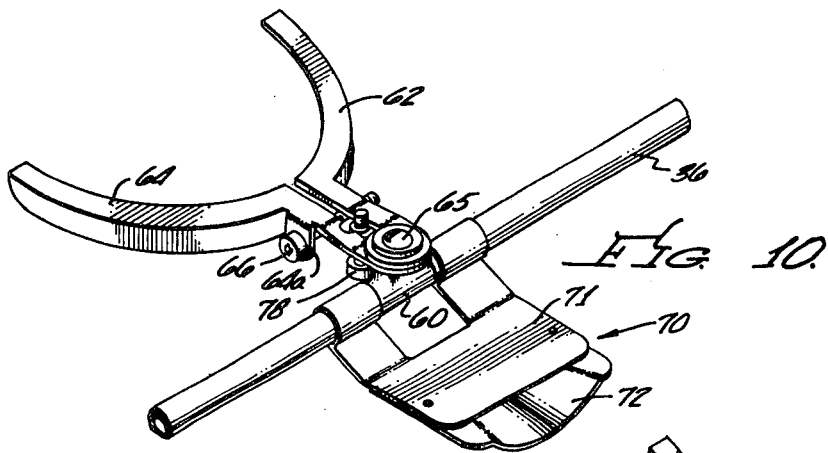
FIG. 10 is an enlarged perspective view of the tooth separator of the lower frame with the separator in the position it occupies outside of the patient's mouth.

As may be seen from FIG. 10, the separator may be swung out of operating position, or may be positioned in operating position as shown in FIG. 11. In this latter position, the base plate 70 is supported by an adjustable screw 78 which is threadedly mounted in the strut portion of the clutch element 64.

Referring to FIG. 14, there is shown a straight edge tool 80 to be used with the upper frame for marking the horizontal plane of reference for the jaw movements measured. As can be seen, the tool has a generally U-shape formed by two L-shaped flat plates 81 and 82. The right plate 81 as seen in FIG. 14 has a recess 83 in its transverse leg 81a which receives the transverse leg 82a of the left plate. The depth of the recess is equal to the thickness of the left plate so that the upper surfaces of the two plates are in the same plane. The recess 83 in the right plate permits lateral adjustment of the plates so as to vary the distance between the rearwardly extending parallel legs 81b and 82b of the plate. To lock the plates at the selected position, there is provided an elongated slot 84 in each of the overlapping legs 81a and 82a of the plates with said slots being aligned so that a bolt 85 extends through the slots and a locking nut 86 is threaded onto the bolt to clamp the plates to each other.

A pointer receiving element 88 is clamped to the tool by means of another nut 89 and bolt 80 combination extending through the slots 84 in the left and right plates. Thus, the element is laterally adjustable by moving the bolt 90 laterally. The element also has an elongated slot 91 formed therein which permits it to be adjustable from front to rear, or angularly. Formed in one edge of a depending lug at the forward end of the element 88 is a dimple 92 for receiving the pointer 33 on the upper frame. As can be seen from FIG. 15, the center 92a of the dimple is precisely aligned with the upper surface of the plate of U-shaped tool 80 so that the dimple is in the same plane with the upper surface.

Operation

As the first step for utilizing the apparatus of the invention, the lower frame 14 without the side arms 38 is attached to the patient's mandible. The clutch elements 62 and 64 shown in FIG. 10 are laterally adjusted by means of the adjusting screw 66 to fit the patient's lower jaw. The tooth separator 70 should be swung to the position shown in FIG. 10 where it is not in operating position. The lower side of the clutch elements 64 and 62 which extend into the patient's mouth is then filled with a denture compound or plastic. While the compound is still pliable the clutch is inserted into the mouth over the lower teeth so that the compound is pressed onto the buccal surfaces of the teeth. After the compound hardens the clutch may be removed from the teeth. Denture paste is then inserted into the compound and the clutch is reinserted over the lower teeth. After several minutes, the paste will have hardened so that the clutch attached to the transverse rod 36 is securely fixed to the teeth.

The upper frame 12 is now positioned on the patient. The set screws 21 and 22 are loosened so that the apparatus may be positioned over the patient's head. The nasion positioner 28 is rotated to fit the particular shape of the nose. The patient holds the nasion positioner against the nose while the operator moves the side arms 15 and 16 inwardly towards the patient's head and front to back, until the grid plates 24 are positioned just in front of the ears and the side arms fit snuggly against the side of the head. The rear portion of the side arms rest next to the head on top of the ear. The set screws 21 and 22 are now tightened in this position to hold the side arms in fixed relation perpendicular to the transverse rod 20. The elastic strap 26 attached to the ends of the side arms is positioned around the back of the head to help hold the upper frame in proper position.

The pointer 33 which is previously loosened on its mount is moved transversely to engage the patient's nose a predetermined distance below the transverse rod 20, and the pointer is then locked in such position.

The adjustable side arms 38 of the lower frame 14 are now slid onto the lower transverse rod 36 and moved inwardly until the writing elements 48 engage the grid on the recording plates 24. Note that the lateral or outer ends of the scribe holders 47 must be spaced sufficiently from the stylus supports 44 to allow for lateral jaw movements. Four to five millimeters should accommodate any such movement.

As a next step, the patient's hinge axis in centric relation position should be located. The tooth separator 70 is swung inwardly into the patient's mouth so that the patient's upper front teeth or ridge will engage the upper surface of the curved separator element 72 as may be seen in FIG. 14. The patient's mandible is opened and closed while in the terminal hinge position, that is, where the lower jaw is in its most rearward position. It is important that the back teeth be slightly separated in that the muscles of the jaws tend to draw the lower jaw into its rearwardmost position, but the rear teeth could act as a fulcrum and interfere with this action if the upper and lower teeth are not separated. Thus it would be more difficult to keep the lower jaw in its hinge axis position.

As the patient's mandible is moved up and down in the terminal hinge position, the side arms 38 of the lower face bow 14 should be adjusted vertically and from front to back until the writing elements, or scribes 48 no longer arc, but simply rotate. The grid lines on the plates 24 are helpful in this step as they act as references. This is the point where the hinge axis exits from the head and is the starting point for the recording measurements. Consequently, with the side arms 38 so positioned, the set screws for positioning the side arms are locked so that the scribes 48 are fixed in aligned relation with the patient's hinge axis. This point is illustrated at 93 in FIG. 20.

To measure the protrusive movement, the patient's mandible is placed in the terminal hinge position or centric relation position and the two axis styluses 45 are pushed inwardly so that the scribes 48 are tightly against the grid plates 24. The styluses are then locked with the set screws 46. The patient then protrudes the lower jaw while the two scribes 48 trace a path P of the protrusive movement on the grids. Since the upper wall of the human temporomandibular joint usually slopes downwardly, the patient's condyles will usually move downwardly as they move forward. This is indicated in phantom lines in FIG. 15. Because of movement in this fashion, the path P traced on the grids slopes or curves downwardly as shown in FIG. 20. The slope of this downward and forward curve may be read on a suitable reference line on the grid.

While the angle of protrusive movement may be measured with respect to a horizontal line on the grid which is parallel to the side arms of the upper frame, it is preferable that the angle be measured with respect to the true horizontal plane of reference formed by the terminal hinge axis position and the point which is located on the side of the patient's nose by the pointer 33. This is preferred because this is the reference plane used for mounting denture casts in an articulator.

Figure 18:
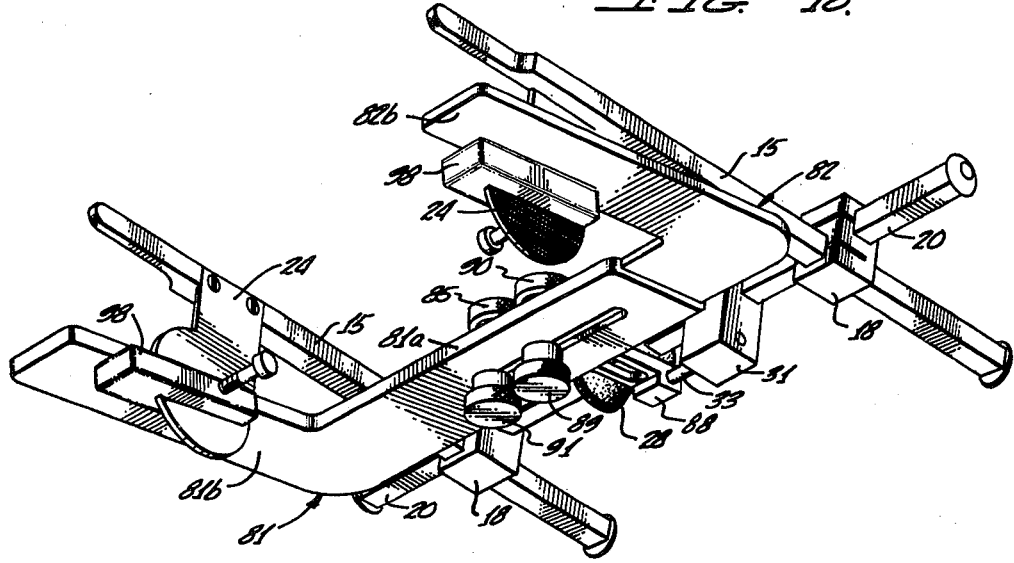
FIG. 18 is a lower perspective view of the horizontal reference plane tool positioned on the upper frame.
Figure 19:
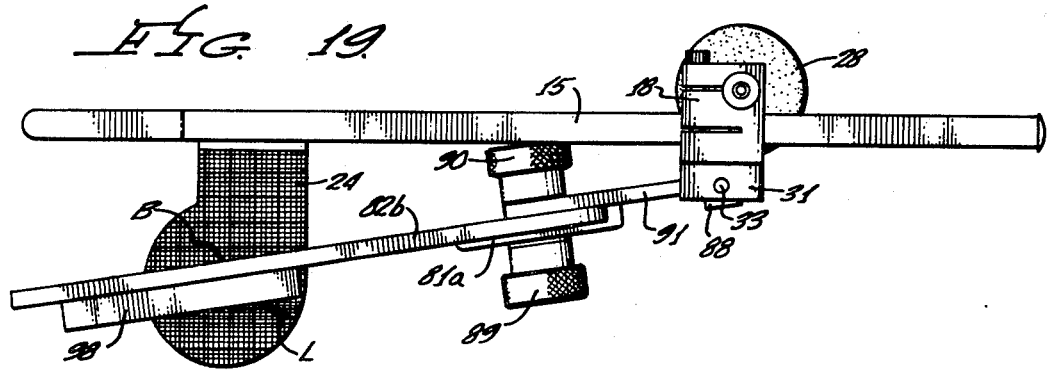
FIG. 19 is a side elevational view of the horizontal reference plane tool on the upper frame.

The reference plane straight edge or tool 80 is used to physically mark the plane on the grid paper on the plates 24, as shown in FIGS. 18 and 19. More specifically, after the protrusive and lateral jaw movement curves P and L, FIG. 20, are marked on the grids, the upper frame 12 is removed from the patient and the U-shaped reference plane tool 80 is positioned to straddle the arms 15 and the recording plates 24 on the upper frame. The legs of the U-shaped tool are laterally adjusted so that they just engage the outer sides of the recording plates 24. The pointer 33 is positioned in the dimple 92 formed in the element 88 attached to the reference plane tool. Note that the element 88 can be adjusted laterally and rearwardly to easily receive the pointer. With the forward end of the tool so positioned by the pointer, one leg of the tool is aligned on the recording plate 24 which it engages so that the hinge axis point 93 is in the reference plane forming the upper surface of the tool. The tool is temporarily clamped in this position by a suitable clamp 98 shown in FIG. 16. The other leg of the tool is then similarly positioned on the other recording plate. By using the tool as a straight edge, a line 95 can then easily be drawn on the grid paper on the recording plate through the hinge axis 93 to represent the reference plane, shown as 95a in FIG. 17. Such a reference line 95 can be marked on both the grids. The reference plane tool 80 is then removed so that the protrusive angle can be readily measured with a protractor 96 or other similar tool.

It will be noted that the slope of the protrusive curve P changes. Thus, it can be measured at any number of points as desired or can be constantly monitored. If comparisons are desired between recording plates of various patients, a standard measurement point with respect to the hinge axis point 93 can be selected.

Referring to FIGS. 8 and 9, another measurement to make is the side shift or lateral displacement of the condyles when the jaw is moved to one side as in chewing. First, the mandible is placed in centric relation position. Second, the stylus is pushed inwardly until the writing tip touches the recording plate. Third, the adjustable screw 46 is tightened to lock the stylus 45 and the marker 50 is slid inwardly on the stylus 45 until it is engaging the outer or lateral surface 44a of the holder 44, as seen in FIG. 8. Next, the adjustable screw 46 locking the stylus 45 with respect to the holder 44 is loosened on one side of the lower frame. The mandible is then moved directly laterally to the extent possible in the direction to move the side of the lower frame on which the screw 46 has been loosened toward the adjacent recording plate. In other words, referring to FIG. 9, the arm 38 is moved, as indicated by the arrow, toward the recording plate 24. The stylus 45 cannot move in that direction because its inner end 48 is in engagement with the plate 24 on the fixed upper frame. Instead, the holder 44 on the arm 38 slides inwardly on the stylus 45. The marker 50 remains fixed on the stylus 45 and thus the reference surface 44a is spaced from the marker 50. It is a simple matter to measure the displacement 53 of the holder 44 which represents the direct or immediate mandibular side shift in one direction. A similar procedure is followed to obtain the side shift in the other direction.

Also the so-called full mandibular side shift is obtained in this manner but the mandible is allowed to make a more complete side chewing movement. During a full chewing movement, the mandible moves forwardly as well as laterally. The border of this combined movement can be recorded by having the stylus 45 trace the path of the hinge axis motion on the vertical plates simultaneously with the side shift measurement. For this purpose, an elastic or small spring 98 shown schematically in FIG. 8a is employed to urge the stylus against the plate at all times so that a tracing is obtained. The elastic 98 extends between the holder 44 and the outer element 51 tightly mounted on the stylus 45. Referring to FIG. 20, the path L of this full chewing movement usually has a steeper slope than that of the protrusive movement P.

As the hinge axis moves during a side chewing movement producing downward and forward slope on one side of the head as evidenced by the path L, the stylus on the other side of the head representing movement of the other end of the hinge axis is moved upwardly and rearwardly a small amount. This path which is shown on FIG. 20 as B and often referred to as backlash, is caused because the tip of the scribe recording the path is spaced laterally from the condyles within the head.

While the border path of the side chewing movement is being recorded on the grid record plate 24, the complete side displacement is being measured by the markers 50 being displaced relative to the reference surfaces 44a on the holders 44. By returning the mandible back to centric position, the displacement is easily measured. This displacement is shown at 55 in FIG. 9a as typically being considerably greater than the immediate side shift 53 in FIG. 9.

The jaw movement information obtained is useful for properly adjusting dental articulators which are utilized to simulate jaw movements. Examples of such use are further explained in the above-identified parent application.

What is claimed is:

1. Dental apparatus comprising:
    a dental clutch to be mounted on the teeth or gums of one of a patient's jaws; and
    a tooth separator supported solely by said clutch including a separator plate positioned on the forward position of said clutch, said separator plate having a smoothly arched surface to be engaged by the teeth or gums of the patient's other jaw the height of said plate being such as to separate the back teeth of said other jaw from the clutch sufficiently to prevent interference of said back teeth with said clutch and the teeth of said one jaw during lateral mandibular movement relative to said other jaw, said surface being arched from side to side with the center of said arch being near the center of the clutch and the curvature of said surface being on a relatively large radius so that said movement with the edges of the teeth of said other jaw engaging said surface is smooth and without jerky vertical movement.

2. The apparatus of claim 1 including:
    a support attached to said clutch and extending forwardly to be positioned outside of a patient's mouth when the clutch is in position; and
    means connecting said plate to said support in a manner to permit said plate to be readily swung into or out of the patient's mouth when said clutch is in position on said one jaw.

3. The apparatus of claim 1 including adjustment means for raising or lowering the position of said plate with respect to said clutch.

4. The apparatus of claim 1 including a strut attached to said clutch and extending forwardly out of said patient's mouth when said clutch is positioned on said one jaw and adjustment means supported on said strut for raising or lowering the vertical position of said separator plate with respect to said clutch.

5. The apparatus of claim 1 including:
    a strut attached to said clutch and extending forwardly from said clutch and out said patient's mouth when the clutch is mounted on said one jaw; and
    a rod supported on said strut to extend horizontally in front of the patient's mouth, and means swingably mounted on said rod for supporting said plate in a manner to permit the plate to be easily swung into or out of the patient's mouth.

6. Dental apparatus comprising:
    a frame member;
    means for supporting said frame member on a patient's mandible adjacent his mouth in fixed relation to the mandible; and
    separator means movably mounted on said member in a manner to be positioned in a patient's mouth to engage the patient's front maxillary teeth or gum to separate the patient's upper and lower back teeth or to be positioned outside of the patient's mouth while said member remains supported in fixed relation on the mandible by said supporting means, said separator means including a separator plate having an upwardly facing smoothly curved surface to be engaged by the patient's front upper teeth, the curvature of said surface being on a relatively large radius so that during lateral mandibular movement with the upper teeth engaging said surface, the plate glides smoothly beneath the teeth, the width of said curved surface being greater than the width of the patient's two upper central incisors.

7. Dental apparatus comprising:
    a transverse rod for extending in front of a patient's mouth;
    a clutch attached to said transverse rod for connecting the frame to a patient's mandibular teeth or gums;
    a separator pivotally mounted on said transverse rod to be swung vertically about said transverse rod into or out of a position in the forward portion of a patient's mouth above the forward portion of said clutch separating the patient's mandible and maxilla, or a position outside of the patient's mouth while said clutch is attached to the patient's mandibular teeth or gums.

8. The apparatus of claim 7 including a strut connecting the clutch to said transverse rod and wherein said separator is supported by said strut when the separator is positioned in the patient's mouth.

9. The apparatus of claim 8 including an adjusting screw threadedly mounted in said strut to provide an adjustable support for the separator.

10. The apperature of claim 7 wherein said separator includes an upper surface for engaging the patient's maxilla or upper front teeth which is separately adjustable from the rest of the separator.

11. The apparatus of claim 8 wherein said separator includes two arms which straddle said strut and are pivotally mounted on said rod.

* * * * *